United States Patent
Dragic et al.

(10) Patent No.: US 9,663,797 B2
(45) Date of Patent: May 30, 2017

(54) OPTIMIZED EXPRESSION CASSETTE FOR EXPRESSING A POLYPEPTIDE WITH HIGH YIELD

(71) Applicants: Zorica Dragic, Basel (CH); Sabine Geisse, Weil am Rhein (DE); Rita Schmitz, Saint-Marcet (FR); Burkhard Wilms, Weil am Rhein (DE)

(72) Inventors: Zorica Dragic, Basel (CH); Sabine Geisse, Weil am Rhein (DE); Rita Schmitz, Saint-Marcet (FR); Burkhard Wilms, Weil am Rhein (DE)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/443,863

(22) PCT Filed: Nov. 18, 2013

(86) PCT No.: PCT/EP2013/074114
§ 371 (c)(1),
(2) Date: May 19, 2015

(87) PCT Pub. No.: WO2014/079819
PCT Pub. Date: May 30, 2014

(65) Prior Publication Data
US 2016/0186206 A1    Jun. 30, 2016

Related U.S. Application Data

(60) Provisional application No. 61/728,459, filed on Nov. 20, 2012.

(51) Int. Cl.
*C12N 15/85* (2006.01)
*C07K 16/00* (2006.01)

(52) U.S. Cl.
CPC ............ *C12N 15/85* (2013.01); *C07K 16/00* (2013.01); *C12N 2830/00* (2013.01); *C12N 2830/30* (2013.01)

(58) Field of Classification Search
None
See application file for complete search history.

(56) References Cited

FOREIGN PATENT DOCUMENTS

| CN | 101903523 A | 12/2010 | |
|---|---|---|---|
| DE | WO 2009080720 A1 * | 7/2009 | ............ C12N 15/85 |
| EP | 1788088 A1 | 5/2007 | |
| WO | 2009080720 A1 | 7/2009 | |
| WO | 2010006415 A1 | 1/2010 | |

OTHER PUBLICATIONS

Suen et al., Protein expression and Purification, 2010, vol. 71 pp. 96-102.*
Gurtu et al., Biochemical and Biophysical Research Communications, 1996, vol. 229 pp. 295-298.*
Suen K F et al. Academic Press, San Diego, CA, vol. 71, No. 1, May 1, 2010, pp. 96-102 XP026924341.
Simmons D et al. The Journal of Immunology, the American Association of Immunologists, US, vol. 141, No. 8, Oct. 15, 1988, pp. 2797-2800.
Ka Fai Suen, et al: "Transient expression of an IL-23R extracellular domain Fc fusion protein in Cho vs. Hek cells results in improved plasma exposure" Protein Expression and Purification, 71(2010), pp. 96-102, Jan. 4, 2010.

* cited by examiner

*Primary Examiner* — Mindy G Brown
(74) *Attorney, Agent, or Firm* — Jason Derry

(57) ABSTRACT

The present invention is based on the finding that the combination of a specific 5'UTR polynucleotide sequence (see SEQ ID NO 1) and the hCD33 secretory leader sequence in an expression cassette for expressing a polypeptide of interest results in a surprisingly better expression level of the polypeptide of interest compared to prior art expression cassettes. Based on this finding, the present invention inter alia provides novel expression cassettes, expression vectors and methods for producing a polypeptide of interest with high yield.

14 Claims, No Drawings

SEQUENCE LISTING

```
<160> NUMBER OF SEQ ID NOS: 15

<210> SEQ ID NO 1
<211> LENGTH: 288
<212> TYPE: DNA
<213> ORGANISM: Artificial Sequence
<220> FEATURE:
<223> OTHER INFORMATION: Description of Artificial Sequence: Synthetic
      5' UTR polynucleotide

<400> SEQUENCE: 1
agatcgcctg gagacgccat ccacgctgtt ttgacctcca tagaagacac cgggaccgat      60
ccagcctccg cggccgggaa cggtgcattg gaacgcggat tccccgtgcc aagagtgacg     120
taagtaccgc ctatagagtc tataggccca ccccttggc ttcgttagaa cgcggctaca      180
attaatacat aaccttatgt atcatacaca tacgatttag gtgacactat agaataacat     240
ccactttgcc tttctctcca caggtgtcca ctcccaggtc caactgca                  288

<210> SEQ ID NO 2
<211> LENGTH: 302
<212> TYPE: DNA
<213> ORGANISM: Artificial Sequence
<220> FEATURE:
<223> OTHER INFORMATION: Description of Artificial Sequence: Synthetic
```

5' UTR polynucleotide

<400> SEQUENCE: 2

```
agatcgcctg gagacgccat ccacgctgtt ttgacctcca tagaagacac cgggaccgat      60
ccagcctccg cggccgggaa cggtgcattg gaacgcggat tccccgtgcc aagagtgacg     120
taagtaccgc ctatagagtc tataggccca ccccccttggc ttcgttagaa cgcggctaca     180
attaatacat aaccttatgt atcatacaca tacgatttag gtgacactat agaataacat     240
ccactttgcc tttctctcca caggtgtcca ctcccaggtc caactgcacc tcggttctat     300
cg                                                                    302
```

<210> SEQ ID NO 3
<211> LENGTH: 316
<212> TYPE: DNA
<213> ORGANISM: Artificial Sequence
<220> FEATURE:
<223> OTHER INFORMATION: Description of Artificial Sequence: Synthetic
      5' UTR polynucleotide

<400> SEQUENCE: 3

```
agatcgcctg gagacgccat ccacgctgtt ttgacctcca tagaagacac cgggaccgat      60
ccagcctccg cggccgggaa cggtgcattg gaacgcggat tccccgtgcc aagagtgacg     120
taagtaccgc ctatagagtc tataggccca ccccccttggc ttcgttagaa cgcggctaca     180
attaatacat aaccttatgt atcatacaca tacgatttag gtgacactat agaataacat     240
ccactttgcc tttctctcca caggtgtcca ctcccaggtc caactgcacc tcggttctat     300
cgaaaacgcg tccacc                                                     316
```

<210> SEQ ID NO 4
<211> LENGTH: 352
<212> TYPE: DNA
<213> ORGANISM: Artificial Sequence
<220> FEATURE:
<223> OTHER INFORMATION: Description of Artificial Sequence: Synthetic
      5' UTR polynucleotide

<400> SEQUENCE: 4

```
agatcgcctg gagacgccat ccacgctgtt ttgacctcca tagaagacac cgggaccgat      60
ccagcctccg cggccgggaa cggtgcattg gaacgcggat tccccgtgcc aagagtgacg     120
taagtaccgc ctatagagtc tataggccca ccccccttggc ttcgttagaa cgcggctaca     180
attaatacat aaccttatgt atcatacaca tacgatttag gtgacactat agaataacat     240
ccactttgcc tttctctcca caggtgtcca ctcccaggtc caactgcacc tcggttctat     300
cgcgattgaa ttccccgggg atcctctagg gtgaccgttt ggtgccgcca cc             352
```

<210> SEQ ID NO 5
<211> LENGTH: 327
<212> TYPE: DNA
<213> ORGANISM: Artificial Sequence
<220> FEATURE:
<223> OTHER INFORMATION: Description of Artificial Sequence: Synthetic
      5' UTR polynucleotide

<400> SEQUENCE: 5

```
agatcgcctg gagacgccat ccacgctgtt ttgacctcca tagaagacac cgggaccgat      60
ccagcctccg cggccgggaa cggtgcattg gaacgcggat tccccgtgcc aagagtgacg     120
taagtaccgc ctatagagtc tataggccca ccccccttggc ttcgttagaa cgcggctaca     180
```

```
attaatacat aaccttatgt atcatacaca tacgatttag gtgacactat agaataacat    240
ccactttgcc tttctctcca caggtgtcca ctcccaggtc caactgcacc tcggttctat    300
cgaaaacgcg cctctagagc cgccacc                                        327
```

```
<210> SEQ ID NO 6
<211> LENGTH: 321
<212> TYPE: DNA
<213> ORGANISM: Artificial Sequence
<220> FEATURE:
<223> OTHER INFORMATION: Description of Artificial Sequence: Synthetic
      5' UTR polynucleotide

<400> SEQUENCE: 6
agatcgcctg gagacgccat ccacgctgtt ttgacctcca tagaagacac cgggaccgat     60
ccagcctccg cggccgggaa cggtgcattg gaacgcggat tccccgtgcc aagagtgacg    120
taagtaccgc ctatagagtc tataggccca ccccccttggc ttcgttagaa cgcggctaca   180
attaatacat aaccttatgt atcatacaca tacgatttag gtgacactat agaataacat    240
ccactttgcc tttctctcca caggtgtcca ctcccaggtc caactgcacc tcggttctat    300
cgaaaaacgc gtgccgccac c                                              321
```

```
<210> SEQ ID NO 7
<211> LENGTH: 320
<212> TYPE: DNA
<213> ORGANISM: Artificial Sequence
<220> FEATURE:
<223> OTHER INFORMATION: Description of Artificial Sequence: Synthetic
      5' UTR polynucleotide

<400> SEQUENCE: 7
agatcgcctg gagacgccat ccacgctgtt ttgacctcca tagaagacac cgggaccgat     60
ccagcctccg cggccgggaa cggtgcattg gaacgcggat tccccgtgcc aagagtgacg    120
taagtaccgc ctatagagtc tataggccca ccccccttggc ttcgttagaa cgcggctaca   180
attaatacat aaccttatgt atcatacaca tacgatttag gtgacactat agaataacat    240
ccactttgcc tttctctcca caggtgtcca ctcccaggtc caactgcacc tcggttctat    300
cgaaaacgcg tgccgccacc                                                320
```

```
<210> SEQ ID NO 8
<211> LENGTH: 737
<212> TYPE: DNA
<213> ORGANISM: Human herpesvirus 5

<400> SEQUENCE: 8
tcaatattgg ccattagcca tattattcat tggttatata gcataaatca atattggcta     60
ttggccattg catacgttgt atctatatca taatatgtac atttatattg gctcatgtcc    120
aatatgaccg ccatgttggc attgattatt gactagttat taatagtaat caattacggg    180
gtcattagtt catagcccat atatggagtt ccgcgttaca taacttacgg taaatggccc    240
gcctggctga ccgcccaacg acccccgccc attgacgtca ataatgacgt atgttcccat    300
agtaacgcca atagggactt tccattgacg tcaatgggtg gagtatttac ggtaaactgc    360
ccacttggca gtacatcaag tgtatcatat gccaagtacg ccccctattg acgtcaatga    420
cggtaaatgg cccgcctggc attatgccca gtacatgacc ttatgggact ttcctacttg    480
gcagtacatc tacgtattag tcatcgctat taccatggtg atgcggtttt ggcagtacat    540
caatgggcgt ggatagcggt ttgactcacg gggatttcca agtctccacc ccattgacgt    600
```

```
caatgggagt ttgttttggc accaaaatca acgggacttt ccaaaatgtc gtaacaactc    660
cgccccattg acgcaaatgg gcggtaggcg tgtacggtgg gaggtctata taagcagagc    720
tcgtttagtg aaccgtc                                                   737
```

<210> SEQ ID NO 9
<211> LENGTH: 119
<212> TYPE: DNA
<213> ORGANISM: Mus sp.

<400> SEQUENCE: 9

```
agatcgcctg gagacgccat ccacgctgtt ttgacctcca tagaagacac cgggaccgat     60
ccagcctccg cggccgggaa cggtgcattg aacgcggat tccccgtgcc aagagtgac     119
```

<210> SEQ ID NO 10
<211> LENGTH: 144
<212> TYPE: DNA
<213> ORGANISM: Mus sp.

<400> SEQUENCE: 10

```
gtaagtaccg cctatagagt ctataggccc accccttgg cttcgttaga acgcggctac      60
aattaataca taaccttatg tatcatacac atacgattta ggtgacacta tagaataaca    120
tccactttgc ctttctctcc acag                                           144
```

<210> SEQ ID NO 11
<211> LENGTH: 25
<212> TYPE: DNA
<213> ORGANISM: Mus sp.

<400> SEQUENCE: 11

```
gtgtccactc ccaggtccaa ctgca                                           25
```

<210> SEQ ID NO 12
<211> LENGTH: 16
<212> TYPE: PRT
<213> ORGANISM: Homo sapiens

<400> SEQUENCE: 12

```
Met Pro Leu Leu Leu Leu Leu Pro Leu Leu Trp Ala Gly Ala Leu Ala
1               5                  10                  15
```

<210> SEQ ID NO 13
<211> LENGTH: 18
<212> TYPE: PRT
<213> ORGANISM: Homo sapiens

<400> SEQUENCE: 13

```
Met Pro Leu Leu Leu Leu Leu Pro Leu Leu Trp Ala Gly Ala Leu Ala
1               5                  10                  15

Met Asp
```

<210> SEQ ID NO 14
<211> LENGTH: 39
<212> TYPE: DNA
<213> ORGANISM: Artificial Sequence
<220> FEATURE:
<223> OTHER INFORMATION: Description of Artificial Sequence: Synthetic
      3' UTR oligonucleotide

<400> SEQUENCE: 14

```
gggcggccgc ttcccttag tgagggttaa tgcttcgag                              39
```

```
<210> SEQ ID NO 15
<211> LENGTH: 222
<212> TYPE: DNA
<213> ORGANISM: Artificial Sequence
<220> FEATURE:
<223> OTHER INFORMATION: Description of Artificial Sequence: Synthetic
      poly A site polynucleotide

<400> SEQUENCE: 15
cagacatgat aagatacatt gatgagtttg gacaaaccac aactagaatg cagtgaaaaa        60
aatgctttat ttgtgaaatt tgtgatgcta ttgctttatt tgtaaccatt ataagctgca       120
ataaacaagt taacaacaac aattgcattc attttatgtt tcaggttcag ggggagatgt       180
gggaggtttt ttaaagcaag taaaacctct acaaatgtgg ta                          222
```

US 9,663,797 B2

OPTIMIZED EXPRESSION CASSETTE FOR EXPRESSING A POLYPEPTIDE WITH HIGH YIELD

SEQUENCE LISTING

The instant application contains a Sequence Listing which has been submitted electronically in ASCII format and is hereby incorporated by reference in its entirety. Said ASCII copy, created on Feb. 25, 2016, is named PAT055302-US-PCT_SL.txt and is 7,637 bytes in size.

FIELD OF THE INVENTION

The present invention inter alia relates to an expression cassette suitable for expressing a polypeptide of interest wherein said expression cassette comprises a combination of a specific 5'UTR and the hCD33 secretory leader sequence. It was found that this specific combination of genetic elements surprisingly results in a significant better expression level of the polypeptide of interest compared to combinations of other 5'UTRs with other secretory leader sequences. Therefore, using this expression cassette is advantageous for producing a polypeptide of interest with high yield.

BACKGROUND OF THE INVENTION

The ability to clone and express a polypeptide of interest in large amounts has become increasingly important. The ability to produce and purify high levels of proteins is in particular important in the human pharmaceutical and biotechnological field, for example for producing protein pharmaceuticals as well as in the basic research setting, for example for crystallizing proteins to allow the determination of their three dimensional structure. Proteins that are otherwise difficult to obtain in quantity can be over-expressed in a host cell and subsequently isolated and purified.

The choice of an expression system for the production of recombinant proteins depends on many factors, including cell growth characteristics, expression levels, intracellular and extracellular expression, post-translational modifications and biological activity of the protein of interest, as well as regulatory issues and economic considerations in the production of therapeutic proteins. Key advantages of mammalian cells over other expression systems such as bacteria or yeast are the ability to carry out proper protein folding, complex N-linked glycosylation and authentic O-linked glycosylation, as well as a broad spectrum of other post-translational modifications. Due to the described advantages, eukaryotic and in particular mammalian cells are currently the expression system of choice for producing complex therapeutic proteins such as monoclonal antibodies.

The most common approach to obtain high expressing host cells (also called high producers) is to generate an appropriate expression vector for expressing the product of interest as a first step. The expression vector drives the expression of the polynucleotide encoding the product of interest in the host cell and usually comprises at least one selectable marker for generating the recombinant cell line. Expression vectors used for expressing a polypeptide in a host cell usually comprise besides the polynucleotide encoding the protein of interest transcriptional control elements suitable to drive transcription such as e.g. promoters, enhancers, polyadenylation signals, transcription pausing or termination signals as element of an expression cassette. Furthermore, suitable translational control elements are usually included and operably linked to the polynucleotides to be expressed, such as e.g. appropriate 5'UTRs and 3' UTRs.

To increase the efficiency of such an expression system, different elements are optimized, especially the DNA sequences which contribute to the efficiency of transcription and translation, protein synthesis, correct folding in ER and protein secretion. High yielding expression systems without optimized translation and secretion components could potentially lead to mRNA instability, insufficient protein secretion, and miss-folded (inactive) protein accumulation in the cell cytosol or membrane. Therefore, expression systems enabling stable and consistent translation and secretion of correctly folded proteins into the cell culture medium are of particular interest. Such secretory systems offer the advantages of a stable and efficient mRNA translation; correct protein folding and efficient secretion, simple and fast product purification procedures, as well as an increased yield compared to cytosolic systems. However, the product yields of the majority of the available secretory systems are not yet fully optimized. To improve the productivity and secretion efficiency, one aim is to optimize the secretion signals (also referred to herein as signal peptide or secretory leader sequence), as well as their combination with different 5'UTR sequences in order to obtain a combination of genetic elements that results in the desired high level expression.

The majority of secreted and membrane-bound proteins from either prokaryotic or eukaryotic organisms possess an amino-terminal leader peptide (also referred to as secretory leader sequence or signal peptide) that is cleaved from the nascent precursor polypeptide during biosynthesis. Secretory leader peptides are usually 5 to 60 amino acids long. This sequence is necessary and sufficient for secretion. Analysis of a large number of these secretory leader peptides has revealed a common structural motif that occurs in the absence of significant amino acid sequence homology [Von Heijne, 1981; Perlman et al, 1983]. In general, a secretory leader sequence consists of a positively charged amino terminus (n), a hydrophobic core (h) and a more polar carboxy terminus (c) that defines the signal peptidase cleavage site. The "n" region of the secretory leader peptide is about 5 to 8 amino acids long and is characterized by the presence of basic residues. The "h" region contains 8 to 12 non-polar amino acids that are composed in average of 37% leucine, 15% alanine, 10% valine, 10% phenylalanine, 7% isoleucine and 21% hydrophobic amino acids such as glycine, methionine, proline or trytophane. This region has a high propensity for alpha-helix formation, a conformation which may facilitate interaction with the interior of the lipid bilayer. Studies on the structural features of secretory leader peptides, primarily based on bacterial proteins, have suggested that the "h" region is critical to signal sequence function [Gierasch, 1990]. Disruption of the h region by deletion or by replacement of hydrophobic residues with hydrophilic or charge amino acids leads to loss of signal function, whereas alterations to the "n" region have little effect [Bird et al, 1990]. The carboxy terminus, or cleavage region, is typically about 6 amino acids long. This region is involved in signal peptidase recognition and cleavage, which is usually required to achieve final folding and secretion of the protein.

The 5' UTR (5' untranslated region) is a part of a DNA sequence that is transcribed into mRNA, but not into protein. It usually begins at the transcription initiation, and ends one nucleotide before the start codon. A 5'UTR may contain sequences that regulate the translation efficiency or mRNA stability, binding sites for proteins, regulatory elements, and sequences that promote the initiation of translation. 5'UTR sequences can vary in their length and may comprise a few tenths of nucleotides up to few hundreds or even several thousand nucleotides. In eukaryotes, the median length of the 5'UTR is approximately 100 to 200 nt. The specific role of the 5'UTR and its elements has not been fully elucidated yet, partially also because the sequence is not translated into functional protein. However, it is known that the combination of a specific 5'UTR and a specific secretory leader sequence can strongly improve the translation and secretion efficiency of the production system and thus may increase the expression yield. However, as a plethora 5'UTRs and secretory leader sequences are available, it is a challenge to obtain an efficient combination that indeed improves the expression. Thus, despite the plethora of available expression cassettes and expression vectors, obtaining a robust polypeptide/protein production with a high yield in eukaryotic cells is still challenging.

Therefore, it is the object of the present invention to provide an expression cassette that enables the secretion of a polypeptide of interest with high yield when said expression cassette is introduced into a host cell. Furthermore, it is an object of the present invention to provide an expression vector that allows for the expression of a polypeptide of interest with high yield. Furthermore, it is an object of the present invention to provide a method suitable for expressing a polypeptide of interest with high yield.

SUMMARY OF THE INVENTION

The present invention is based on the finding that combining a specific 5'UTR polynucleotide sequence (see SEQ ID NO 1, which is also contained in SEQ ID NO 2, 3 and 4 and also 5, 6 and 7) and the human CD33 secretory leader sequence in an expression cassette results in a surprisingly high expression of the polypeptide of interest that is encoded by said expression cassette. In several examples, it was shown that the expression cassette according to the present invention is superior over expression cassettes known in the prior art because the expression yield could be increased up to 4 fold. The superior performance of the expression cassette according to the present invention was confirmed in numerous experiments wherein different polypeptides of interest were expressed from said expression cassette. Therefore, the expression cassette according to the present invention is particularly advantageous for producing a polypeptide of interest with high yield. Additionally, it was found that the correct processing of the leader sequence may be improved. Hence, the present invention provides a valuable contribution to the art because this novel design of the expression cassette considerably improves the expression of the polypeptide of interest.

According to a first aspect, the present invention provides an expression cassette for expressing a polypeptide of interest comprising:
a) a promoter
b) a 5'UTR polynucleotide sequence, wherein said 5'UTR polynucleotide sequence is selected from the group consisting of
  i) a 5'UTR polynucleotide sequence comprising the following sequence (SEQ ID NO 1)
agatcgcctggagacgccatccacgctgttttgacctccatagaagacac cgggaccgatccagcctccgcggccgggaacggtgcattggaacgcggat tccccgtgccaagagtgacgtaagtaccgcctatagagtctataggccca ccccottggcttcgttagaacgcggctacaattaatacataaccttatgt atcatacacatacgatttaggtgacactatagaataacatccactttgcc tttctctccacaggtgtccactcccaggtccaactgca;

ii) a 5'UTR polynucleotide sequence comprising the following sequence (SEQ ID NO 2)
agatcgcctggagacgccatccacgctgttttgacctccatagaagacac cgggaccgatccagcctccgcggccgggaacggtgcattggaacgcggat tccccgtgccaagagtgacgtaagtaccgcctatagagtctataggccca ccccottggcttcgttagaacgcggctacaattaatacataaccttatgt atcatacacatacgatttaggtgacactatagaataacatccactttgcc tttctctccacaggtgtccactcccaggtccaactgcacctcggttctat cg;

iii) a 5'UTR polynucleotide sequence comprising the following sequence (SEQ ID NO 3)
agatcgcctggagacgccatccacgctgttttgacctccatagaagacac cgggaccgatccagcctccgcggccgggaacggtgcattggaacgcggat tccccgtgccaagagtgacgtaagtaccgcctatagagtctataggccca ccccottggcttcgttagaacgcggctacaattaatacataaccttatgt atcatacacatacgatttaggtgacactatagaataacatccactttgcc tttctctccacaggtgtccactcccaggtccaactgcacctcggttctat cgaaaacgcgtccacc;

iv) a 5'UTR polynucleotide sequence comprising the following sequence (SEQ ID NO 4)
agatcgcctggagacgccatccacgctgttttgacctccatagaagacac cgggaccgatccagcctccgcggccgggaacggtgcattggaacgcggat tccccgtgccaagagtgacgtaagtaccgcctatagagtctataggccca ccccottggcttcgttagaacgcggctacaattaatacataaccttatgt atcatacacatacgatttaggtgacactatagaataacatccactttgcc tttctctccacaggtgtccactcccaggtccaactgcacctcggttctat cgcgattgaattccccggggatcctctagggtgaccgtttggtgccgcca cc;

v) a 5'UTR polynucleotide sequence comprising the following sequence (SEQ ID NO 5)
agatcgcctggagacgccatccacgctgttttgacctccatagaagacac cgggaccgatccagcctccgcggccgggaacggtgcattggaacgcggat tccccgtgccaagagtgacgtaagtaccgcctatagagtctataggccca -continued
ccccttggcttcgttagaacgcggctacaattaatacataaccttatgt atcatacacatacgatttaggtgacactatagaataacatccactttgcc tttctctccacaggtgtccactcccaggtccaactgcacctcggttctat cgaaaacgcgcctctagagccgccacc;

vi) a 5'UTR polynucleotide sequence comprising the following sequence (SEQ ID NO 6)
agatcgcctggagacgccatccacgctgttttgacctccatagaagacac cgggaccgatccagcctccgcggccgggaacggtgcattggaacgcggat tccccgtgccaagagtgacgtaagtaccgcctatagagtctataggccca ccccttggcttcgttagaacgcggctacaattaatacataaccttatgt atcatacacatacgatttaggtgacactatagaataacatccactttgcc tttctctccacaggtgtccactcccaggtccaactgcacctcggttctat cgaaaaacgcgtgccgccacc;

vii) a 5'UTR polynucleotide sequence comprising the following sequence (SEQ ID NO 7)
agatcgcctggagacgccatccacgctgttttgacctccatagaagacac cgggaccgatccagcctccgcggccgggaacggtgcattggaacgcggat tccccgtgccaagagtgacgtaagtaccgcctatagagtctataggccca ccccttggcttcgttagaacgcggctacaattaatacataaccttatgt atcatacacatacgatttaggtgacactatagaataacatccactttgcc tttctctccacaggtgtccactcccaggtccaactgcacctcggttctat cgaaaacgcgtgccgccacc;

viii) a 5'UTR polynucleotide sequence comprising a sequence that is at least 85%, preferably at least 90% identical to a sequence shown in SEQ ID NO 1, SEQ ID NO 2, SEQ ID NO 3 or SEQ ID NO 4 or SEQ ID NO 5, SEQ ID NO 6 or SEQ ID NO 7;
  c) a polynucleotide encoding a hCD33 secretory leader sequence; and
  d) a polynucleotide encoding a polypeptide of interest or an insertion site for inserting a polynucleotide encoding a polypeptide of interest.

According to a second aspect, the present invention provides an expression vector for expressing a polypeptide of interest, comprising at least one expression cassette according to the first aspect of the present invention.

According to a third aspect, the present invention provides a eukaryotic host cell which comprises at least one expression cassette according to the first aspect of the present invention and/or at least one expression vector according to the second aspect of the present invention.

According to a fourth aspect, the present invention provides a method for producing the host cell according to the third aspect of the present invention, wherein an expression vector according to the second aspect of the present invention is introduced into a eukaryotic host cell.

According to a fifth aspect, the present invention provides a method for producing a polypeptide of interest, said method comprising the culturing of host cells according to the third aspect of the present invention in a cell culture under conditions allowing the expression of said polypeptide of interest.

According to a sixth aspect, the present invention pertains to the use of a 5'UTR sequence in combination with a hCD33 secretory leader sequence in an expression cassette for expressing a polypeptide of interest with high yield from said expression cassette, wherein said 5'UTR polynucleotide sequence is selected from the group consisting of
  i) a 5'UTR polynucleotide sequence comprising the sequence (SEQ ID NO 1)
agatcgcctggagacgccatccacgctgttttgacctccatagaagacac cgggaccgatccagcctccgcggccgggaacggtgcattggaacgcggat tccccgtgccaagagtgacgtaagtaccgcctatagagtctataggccca ccccttggcttcgttagaacgcggctacaattaatacataaccttatgt atcatacacatacgatttaggtgacactatagaataacatccactttgcc tttctctccacaggtgtccactcccaggtccaactgca;

ii) a 5'UTR polynucleotide sequence comprising the following sequence (SEQ ID NO 2)
agatcgcctggagacgccatccacgctgtttgacctccatagaagacac cgggaccgatccagcctccgcggccgggaacggtgcattggaacgcggat tccccgtgccaagagtgacgtaagtaccgcctatagagtctataggccca ccccttggcttcgttagaacgcggctacaattaatacataaccttatgt atcatacacatacgatttaggtgacactatagaataacatccactttgcc tttctctccacaggtgtccactcccaggtccaactgcacctcggttctat cg;

iii) a 5'UTR polynucleotide sequence comprising the following sequence (SEQ ID NO 3)
agatcgcctggagacgccatccacgctgttttgacctccatagaagacac cgggaccgatccagcctccgcggccgggaacggtgcattggaacgcggat tccccgtgccaagagtgacgtaagtaccgcctatagagtctataggccca ccccttggcttcgttagaacgcggctacaattaatacataaccttatgt atcatacacatacgatttaggtgacactatagaataacatccactttgcc tttctctccacaggtgtccactcccaggtccaactgcacctcggttctat cgaaaacgcgtccacc;

iv) a 5'UTR polynucleotide sequence comprising the following sequence (SEQ ID NO 4)
agatcgcctggagacgccatccacgctgttttgacctccatagaagacac cgggaccgatccagcctccgcggccgggaacggtgcattggaacgcggat tccccgtgccaagagtgacgtaagtaccgcctatagagtctataggccca ccccttggcttcgttagaacgcggctacaattaatacataaccttatgt -continued atcatacacatacgatttaggtgacactatagaataacatccactttgcc tttctctccacaggtgtccactcccaggtccaactgcacctcggttctat cgcgattgaattccccggggatcctctagggtgaccgtttggtgccgcca cc;

v) a 5'UTR polynucleotide sequence comprising the following sequence (SEQ ID NO 5)
agatcgcctggagacgccatccacgctgttttgacctccatagaagacac cgggaccgatccagcctccgcggccgggaacggtgcattggaacgcggat tccccgtgccaagagtgacgtaagtaccgcctatagagtctataggccca ccccttggcttcgttagaacgcggctacaattaatacataaccttatgt atcatacacatacgatttaggtgacactatagaataacatccactttgcc tttctctccacaggtgtccactcccaggtccaactgcacctcggttctat cgaaaacgcgcctctagagccgccacc;

vi) a 5'UTR polynucleotide sequence comprising the following sequence (SEQ ID NO 6)
agatcgcctggagacgccatccacgctgttttgacctccatagaagacac cgggaccgatccagcctccgcggccgggaacggtgcattggaacgcggat tccccgtgccaagagtgacgtaagtaccgcctatagagtctataggccca ccccttggcttcgttagaacgcggctacaattaatacataaccttatgt atcatacacatacgatttaggtgacactatagaataacatccactttgcc tttctctccacaggtgtccactcccaggtccaactgcacctcggttctat cgaaaacgcgtgccgccacc;

vii) a 5'UTR polynucleotide sequence comprising the following sequence (SEQ ID NO 7)
agatcgcctggagacgccatccacgctgttttgacctccatagaagacac cgggaccgatccagcctccgcggccgggaacggtgcattggaacgcggat tccccgtgccaagagtgacgtaagtaccgcctatagagtctataggccca ccccttggcttcgttagaacgcggctacaattaatacataaccttatgt atcatacacatacgatttaggtgacactatagaataacatccactttgcc tttctctccacaggtgtccactcccaggtccaactgcacctcggttctat cgaaaacgcgtgccgccacc;

viii) a 5'UTR polynucleotide sequence comprising a sequence that is at least 85%, preferably at least 90% identical to a sequence shown in SEQ ID NO 1, SEQ ID NO 2, SEQ ID NO 3 or SEQ ID NO 4 or SEQ ID NO 5, SEQ ID NO 6 or SEQ ID NO 7.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

DETAILED DESCRIPTION OF THE INVENTION

The present invention provides an expression cassette for expressing a polypeptide of interest comprising a novel combination of genetic elements, namely a specific 5'UTR polynucleotide sequence and the hCD33 secretory leader sequence. This specific combination of genetic elements results in a significant increase in the expression efficiency of the encoded polypeptide of interest. Furthermore, it was found that the processing of the leader sequence may be improved so that unwanted sequence extensions or truncations (also known as "clipping") due to erroneous processing of the leader sequence can be reduced.

According to a first aspect, an expression cassette is provided for expressing a polypeptide of interest comprising:
a) a promoter
b) a 5'UTR polynucleotide sequence, wherein said 5'UTR polynucleotide sequence is selected from the group consisting of
i) a 5'UTR polynucleotide sequence comprising the following sequence (SEQ ID NO 1)
agatcgcctggagacgccatccacgctgttttgacctccatagaagacac cgggaccgatccagcctccgcggccgggaacggtgcattggaacgcggat tccccgtgccaagagtgacgtaagtaccgcctatagagtctataggccca ccccttggcttcgttagaacgcggctacaattaatacataaccttatgt atcatacacatacgatttaggtgacactatagaataacatccactttgcc tttctctccacaggtgtccactcccaggtccaactgca;

ii) a 5'UTR polynucleotide sequence comprising the following sequence (SEQ ID NO 2)
agatcgcctggagacgccatccacgctgttttgacctccatagaagacac cgggaccgatccagcctccgcggccgggaacggtgcattggaacgcggat tccccgtgccaagagtgacgtaagtaccgcctatagagtctataggccca ccccttggcttcgttagaacgcggctacaattaatacataaccttatgt atcatacacatacgatttaggtgacactatagaataacatccactttgcc tttctctccacaggtgtccactcccaggtccaactgcacctcggttctat cg;

iii) a 5'UTR polynucleotide sequence comprising the following sequence (SEQ ID NO 3)
agatcgcctggagacgccatccacgctgttttgacctccatagaagacac cgggaccgatccagcctccgcggccgggaacggtgcattggaacgcggat tccccgtgccaagagtgacgtaagtaccgcctatagagtctataggccca ccccttggcttcgttagaacgcggctacaattaatacataaccttatgt

```
atcatacacatacgatttaggtgacactatagaataacatccactttgcc tttctctccacaggtgtccactcccaggtccaactgcacctcggttctat cgaaaacgcgtccacc;
``` iv) a 5'UTR polynucleotide sequence comprising the following sequence

```
                                          (SEQ ID NO 4)
agatcgcctggagacgccatccacgctgttttgacctccatagaagacac cgggaccgatccagcctccgcggccgggaacggtgcattggaacgcggat tccccgtgccaagagtgacgtaagtaccgcctatagagtctataggccca cccccttggcttcgttagaacgcggctacaattaatacataaccttatgt atcatacacatacgatttaggtgacactatagaataacatccactttgcc tttctctccacaggtgtccactcccaggtccaactgcacctcggttctat cgcgattgaattccccggggatcctctagggtgaccgtttggtgccgcca cc;
``` v) a 5'UTR polynucleotide sequence comprising the following sequence

```
                                          (SEQ ID NO 5)
agatcgcctggagacgccatccacgctgttttgacctccatagaagacac cgggaccgatccagcctccgcggccgggaacggtgcattggaacgcggat tccccgtgccaagagtgacgtaagtaccgcctatagagtctataggccca cccccttggcttcgttagaacgcggctacaattaatacataaccttatgt atcatacacatacgatttaggtgacactatagaataacatccactttgcc tttctctccacaggtgtccactcccaggtccaactgcacctcggttctat cgaaaacgcgcctctagagccgccacc;
``` vi) a 5'UTR polynucleotide sequence comprising the following sequence

```
                                          (SEQ ID NO 6)
agatcgcctggagacgccatccacgctgttttgacctccatagaagacac cgggaccgatccagcctccgcggccgggaacggtgcattggaacgcggat tccccgtgccaagagtgacgtaagtaccgcctatagagtctataggccca cccccttggcttcgttagaacgcggctacaattaatacataaccttatgt atcatacacatacgatttaggtgacactatagaataacatccactttgcc tttctctccacaggtgtccactcccaggtccaactgcacctcggttctat cgaaaacgcgtgccgccacc;
``` vii) a 5'UTR polynucleotide sequence comprising the following sequence

```
                                          (SEQ ID NO 7)
agatcgcctggagacgccatccacgctgttttgacctccatagaagacac cgggaccgatccagcctccgcggccgggaacggtgcattggaacgcggat tccccgtgccaagagtgacgtaagtaccgcctatagagtctataggccca cccccttggcttcgttagaacgcggctacaattaatacataaccttatgt
```

```
atcatacacatacgatttaggtgacactatagaataacatccactttgcc tttctctccacaggtgtccactcccaggtccaactgcacctcggttctat cgaaaacgcgtgccgccacc;
``` viii) a 5'UTR polynucleotide sequence comprising a sequence that is at least 85%, preferably at least 90% identical to a sequence shown in SEQ ID NO 1, SEQ ID NO 2, SEQ ID NO 3 or SEQ ID NO 4 or SEQ ID NO 5, SEQ ID NO 6 or SEQ ID NO 7;

c) a polynucleotide encoding a hCD33 secretory leader sequence; and d) a polynucleotide encoding a polypeptide of interest or an insertion site for inserting a polynucleotide encoding a polypeptide of interest.

The term "expression cassette" as used herein in particular refers to a DNA segment that is capable in an appropriate setting of driving the expression of a polynucleotide encoding a polypeptide of interest that is incorporated in said expression cassette. When introduced into a host cell, an expression cassette inter alia is capable of directing the cell's machinery to transcribe an incorporated polynucleotide encoding a polypeptide of interest into RNA, which is then usually further processed and finally translated into the polypeptide of interest. The expression cassette can be comprised in an expression vector as will be described in further detail below. The individual elements of the expression cassette according to the present invention are subsequently explained in detail.

The expression cassette according to the present invention comprises as element a) a promoter. The term "promoter" as used herein in particular refers to a DNA element that facilitates the transcription of a polynucleotide the promoter is operably linked to. The promoter may also form part of a promoter/enhancer element. Although the physical boundaries between the elements "promoter" and "enhancer" are not always clear, the term "promoter" usually refers to a site on the nucleic acid molecule to which an RNA polymerase and/or any associated factors binds and at which transcription is initiated. Enhancers potentiate promoter activity, temporally as well as spatially. Many promoters are known in the prior art that are transcriptionally active in a wide range of cell types. Promoters can be divided in two classes, those that function constitutively and those that are regulated by induction or derepression. Both classes are suitable for protein expression. Promoters that are used for high-level production of polypeptides in eukaryotic and in particular mammalian cells should be strong and preferably should be active in a wide range of cell types. Strong constitutive promoters which are capable of driving the expression in many cell types are well known in the prior art and thus, need no to detailed description here. Preferably, a cytomegalovirus (CMV) promoter is used according to the teachings of the present invention. A promoter or promoter/enhancer derived from the immediate early (IE) region of the human cytomegalovirus (hCMV) is particularly suitable as promoter in the expression cassette according to the present invention. The immediate early (IE) region of the human cytomegalovirus (hCMV) and functional expression promoting fragments and/or functional expression enhancing fragments derived therefrom are e.g. described in EP 0 173 177 and EP 0 323 997 and are also well-known in the prior art. Thus, several fragments of the immediate early (IE) region of hCMV can be used as promoter and/or promoter/enhancer. According to one embodiment a human CMV promoter is used in the expression cassette according to the present invention. The term "a human CMV promoter" as used herein in particular refers to a promoter that is derived from the immediate early (IE) region of hCMV.

According to one embodiment, a human CMV promoter is used which is selected from the group consisting of:
a) a promoter comprising the following sequence (SEQ ID NO 8)
```
tcaatattgg ccattagcca tattattcat tggttatata gcataaatca atattggcta ttggccattg catacgttgt atctatatca taatatgtac atttatattg gctcatgtcc aatatgaccg ccatgttggc attgattatt gactagttat taatagtaat caattacggg gtcattagtt catagcccat atatggagtt ccgcgttaca taacttacgg taaatggccc gcctggctga ccgcccaacg accccgccc attgacgtca ataatgacgt atgttcccat agtaacgcca atagggactt tccattgacg tcaatgggtg gagtatttac ggtaaactgc ccacttggca gtacatcaag tgtatcatat gccaagtacg cccctattg acgtcaatga cggtaaatgg cccgcctggc attatgccca gtacatgacc ttatgggact ttcctacttg gcagtacatc tacgtattag tcatcgctat taccatggtg atgcggtttt ggcagtacat caatgggcgt ggatagcggt ttgactcacg gggatttcca agtctccacc ccattgacgt caatgggagt ttgttttggc accaaaatca acgggacttt ccaaaatgtc gtaacaactc cgccccattg acgcaaatgg gcggtaggcg tgtacggtgg gaggtctata taagcagagc tcgtttagtg aaccgtc;
```
or a functional fragment thereof which functions as promoter;
b) a promoter comprising a sequence that is at least 80%, preferably at least 85%, more preferably at least 90%, more preferably at least 95%, more preferred at least 97%, most preferred at least 99% identical to the sequence shown in SEQ ID NO 8 or a functional fragment thereof which functions as promoter.

The % identity may be calculated over the whole length of the reference sequence.

It was found that a respective promoter works particularly well in combination with the specific 5'UTR polynucleotide sequence selected from the above group and the hCD33 signal sequence as is taught by the present invention.

The expression cassette according to the present invention further comprises as element b) a specific 5'UTR (five prime untranslated region) polynucleotide sequence. The term a "5'UTR polynucleotide sequence" as used herein in particular refers to a DNA sequence that is transcribed into mRNA but is subsequently not translated into a polypeptide. A 5'UTR polynucleotide sequence usually starts at the transcription start site and ends before the start codon of the actual coding region. In the expression cassette according to the present invention, the 5'UTR polynucleotide sequence ends before the polynucleotide encoding the hCD33 secretory leader sequence starts.

The 5'UTR polynucleotide sequence used in the expression cassette according to the present invention preferably comprises the sequence shown in SEQ ID NO 1. A respective 5'UTR polynucleotide sequence is described in WO 2009/080720.

According to one embodiment, the 5'UTR polynucleotide sequence comprises a sequence selected from the sequences SEQ ID NO 1, SEQ ID NO 2, SEQ ID NO 3 and SEQ ID NO 4 or comprises a sequence selected from the sequences SEQ ID NO 5, SEQ ID NO 6 or SEQ ID NO 7. The 5' UTR sequence that is shown in SEQ ID NO 1 is a consensus sequence that is also comprised in the 5' UTR sequences shown as SEQ ID NO 2, 3 and 4 as well as in the 5'UTR sequences shown as SEQ ID NO 5, 6 and 7. Preferably, the 5'UTR sequence comprising or consisting of SEQ ID NO 3 is used for expressing the light chain of an antibody or a functional fragment thereof and the 5'UTR sequence comprising or consisting of SEQ ID NO 1 or SEQ ID NO 4 is used for expressing the heavy chain of an antibody or a functional fragment thereof. The 5'UTR sequence comprising or consisting of SEQ ID NO: 5 is according to one embodiment used for expressing the light chain of an antibody or a functional fragment thereof. SEQ ID NO 5 may also be used for example for the expression of a nanobody as exemplary embodiment. The 5'UTR sequence comprising or consisting of SEQ ID NO: 6 is according to one embodiment used for expressing the heavy chain of an antibody or a functional fragment thereof. The 5'UTR sequence comprising or consisting of SEQ ID NO: 7 is according to one embodiment used for expressing the heavy chain of an antibody or a functional fragment thereof. It was also tested in the examples.

It was found that the 5'UTR that is used according to the present invention is composed of several elements and comprises an intron flanking region 5' sequence, an intron and an intron flanking region 3' sequence. The intron and intron flanking regions comprised in said 5'UTR originate from mouse IgG heavy chain (see e.g. Eaton et al., 1986, Biochemistry 25, 8343-8347, Neuberger et al., 1983, EMBO J. 2(8), 1373-1378; it can be obtained from the pRK-5 vector (BD PharMingen)). The following table illustrates the putative boundaries of said elements that are comprised in the 5'UTR that can be used according to the present invention:

```
Intron flanking region 5' sequence
                                     (SEQ ID NO 9)
agatcgcctggagacgccatccacgctgttttgacctccatagaagaca ccgggaccgatccagcctccgcggccgggaacggtgcattggaacg cggattccccgtgccaagagtgac Intron
                                     (SEQ ID NO 10)
gtaagtaccgcctatagagtctataggcccaccccttggcttcgttag aacgcggctacaattaatacataaccttatgtatcatacacatacgatt taggtgacactatagaataacatccactttgcctttctctccacag Intron flanking region 3' sequence
                                     (SEQ ID NO 11)
gtgtccactcccaggtccaactgca
```

Furthermore, a 5'UTR polynucleotide sequence can be used which comprises a sequence that is at least 85%, preferably at least 90%, preferably at least 95%, more preferred at least 98%, most preferred at least 99% identical to the sequence shown in SEQ ID NOs 1, 2, 3 or 4 or the sequence shown in SEQ ID NO 5, SEQ ID NO 6 or SEQ ID NO 7. The identity may be calculated over the whole length of the reference 5'UTR sequence.

In numerous experiments the inventors found that said particular 5'UTR polynucleotide sequences have in combination with the hCD33 signal sequence the above described advantageous effects on the expression yield which is substantially increased compared to prior art expression cassettes.

The expression cassette according to the present invention further comprises as element c) a polynucleotide encoding an hCD33 secretory leader sequence. Human CD33 is a member of the sialic acid-binding immunoglobulin-like lectin inhibitory receptors. CD33 is a 67-kDa transmembrane glycoprotein and is specifically expressed on the myeloid lineage. The term "a polynucleotide encoding a hCD33 secretory leader sequence" as used herein in particular refers to a polynucleotide that encodes a secretory leader sequence comprising the hCD33 secretory leader sequence. Thus, upon transcription and subsequent translation a secretory leader sequence is obtained which comprises and preferably consists of a hCD33 secretory leader sequence. Said secretory leader sequence has the effect that a polypeptide of interest fused thereto is efficiently secreted from the host cell. The secretory leader sequence is cleaved off during biosynthesis. As discussed above, it was surprisingly found by the inventors that the specific combination of the above described 5'UTR polynucleotide sequence with an hCD33 secretory leader sequence results in a remarkable increase of polypeptide expression. Thus, the combination according to the present invention is superior to other combinations which use the same 5'UTR in conjunction with other secretory leader sequences which do not comprise an hCD33 secretory leader sequence but e.g. an immunoglobulin secretory leader sequence as is described in WO2009/080720. According to one embodiment, the hCD33 secretory leader sequence used in the expression cassette according to the present invention comprises the following amino acid sequence:

(SEQ ID NO 12)
MPLLLLLPLLWAGALA

Different amino acid sequences are described in the literature for the hCD33 secretory leader sequence. Most documents describe the hCD33 secretory leader sequence as consisting of the following amino acid sequence (SEQ ID NO 13)
MPLLLLLPLLWAGALAMD.

As becomes apparent, the SEQ ID NO 13 comprises two additional amino acids at the 3' end compared to SEQ ID NO 12. According to one embodiment, the polynucleotide encoding an hCD33 secretory leader sequence encodes a secretory leader sequence consisting of the amino acid sequence shown in SEQ ID NO 12 or SEQ ID NO 13. However, it is preferred to use the shorter hCD33 secretory leader sequence shown in SEQ ID NO 12.

The slightly shorter signal sequence is assumed to enhance the probability of correct peptidase cleavage, enables correct processing and thereby ensures product quality. Using the longer CD33 secretory leader sequence shown in SEQ ID NO 13 could pose the risk that the polypeptide of interest carries additional amino acids at their N-terminus after the secretory leader sequence is cleaved off, what is unacceptable in particular when expressing pharmaceutical polypeptides. This risk is avoided when using the hCD33 secretory leader sequence shown in SEQ ID NO 12. Furthermore, the shorter sequence is apparently more efficient for secretion due to a better charge distribution, in particular when used in combination with the 5'UTR polynucleotide sequence according to the present invention. Thus, preferably, the polynucleotide encodes an hCD33 secretory leader sequence that consists of the amino acid sequence shown in SEQ ID NO 12.

In the expression cassette, the promoter (element a)) is arranged 5' from the 5'UTR polynucleotide sequence (element b) which in turn is arranged 5' from the polynucleotide encoding the hCD33 secretory leader sequence (element c)). Said elements are operably linked in the expression cassette in order to allow an efficient expression of a polypeptide of interest if a polynucleotide encoding a respective polypeptide of interest is inserted into said expression cassette.

The expression cassette according to the present invention is "suitable for expressing a polypeptide of interest". This term in particular describes that a polypeptide is expressed from said expression cassette if a polynucleotide encoding said polypeptide is inserted into said expression cassette. Thus, according to one embodiment the expression cassette according to the present invention comprises as element d) a polynucleotide encoding a polypeptide of interest. Thus, said polynucleotide comprises the coding region of the polypeptide of interest. Preferably, said polynucleotide is or is derived from a cDNA. Preferably, said polynucleotide does not comprise an additional secretory leader sequence. Said polynucleotide encoding the polypeptide of interest is located 3' from the polynucleotide encoding the hCD33 secretory leader sequence, so that upon expression a fusion polypeptide is obtained which comprises the hCD33 secretory leader sequence and the polypeptide of interest. The 5'UTR and the secretory leader sequence that is used in the expression cassette according to the present invention are heterologous to the polynucleotide encoding the polypeptide of interest, i.e. they are not naturally associated with said polynucleotide. The expression of the polynucleotide encoding the polypeptide of interest is under the post-transcriptional control of said 5'UTR and said secretory leader sequence comprising and preferably consisting of the hCD33 leader sequence.

According to an alternative embodiment, the expression cassette comprises an insertion site for inserting a polynucleotide encoding a polypeptide of interest however, does not yet comprise a polynucleotide encoding a polypeptide of interest. Said insertion site is located 3' from the polynucleotide encoding the hCD33 secretory leader sequence. For this purpose the expression cassette may comprise e.g. a multiple cloning site (MCS) which can e.g. be used in all reading frames. A respective "empty" expression cassette comprising an insertion site can be used for inserting a polynucleotide encoding a desired polypeptide of interest.

This has the advantage that a customer can insert a polynucleotide encoding a desired polypeptide into said insertion site thereby completing the expression cassette. Upon expression, the desired polypeptide fused to the secretory leader sequence according to the present invention is expressed from said completed expression cassette and secreted. Thus, a respective "empty" expression cassette provides a useful tool for expressing different polypeptides of interest because the expression cassette can be easily adapted to the intended use simply by inserting the polynucleotide encoding the desired polypeptide of interest into the insertion site.

Furthermore, the expression cassette may comprise an appropriate transcription termination site. Transcription termination sites are well characterized in the prior art and their incorporation in expression cassettes has been shown to have multiple beneficial effects on gene expression. As will be described in further detail below, the expression cassette according to the present invention is in particular intended for expressing a polypeptide of interest in a eukaryotic host cell. Most eukaryotic nascent mRNAs possess a poly A tail at their 3' end which is added during a complex process that involves cleavage of the primary transcript and a coupled polyadenylation reaction. The polyA tail is inter alia advantageous for mRNA stability. Hence, the expression cassette preferably comprises respectively provides a polyadenylation site suitable for transcription termination and polyadenylation. There are several efficient polyA signals that can be used in expression cassettes that are intended for expression in eukaryotic cells, including those derived from bovine growth hormone (bgh), mouse beta-globin, the SV40 early transcription unit and the Herpes simplex virus thymidine kinase gene. However, also synthetic polyadenylation sites are known (see e.g. the pCl-neo expression vector of Promega which is based on Levitt el al, 1989, Genes Dev. 3, (7): 1019-1025). Thus, the polyadenylation site that is used in the expression cassette according to the present invention can be selected from the group consisting of SV40polyA site, such as the SV40 late and early poly-A site (see e.g. plasmid pSV2-DHFR as described in Subramani et al, 1981, Mol. Cell. Biol. 854-864), a synthetic polyA site (see e.g. the pCl-neo expression vector of Promega which is based on Levitt el al, 1989, Genes Dev. 3, (7): 1019-1025) and a bgh polyA site (bovine growth hormone). The transcription termination site can be provided together with the polynucleotide encoding the polypeptide of interest or can be provided as separate element in the expression cassette.

Thus, according to one embodiment, the expression cassette further comprises a 3'UTR sequence as element e). A three prime untranslated region (3'UTR) follows the coding region and comprises regulatory elements. Elements that may be comprised in said 3'UTR include but are not limited to binding sites for proteins and/or molecules that induce RNAi, such as miRNAs. According to one embodiment, a 3' UTR comprising the following sequence is used:

(SEQ ID NO 14)
gggcggccgcttccctttagtgagggttaatgcttcgag.

Furthermore, the expression cassette may comprise a polyadenylation signal as element f). Suitable polyadenylation sites are described above. According to one embodiment, a poly A site is used, comprising the following sequence:

(SEQ ID NO 15)
cagacatgataagatacattgatgagtttggacaaaccacaactagaatg cagtgaaaaaaatgctttatttgtgaaatttgtgatgctattgctttatt tgtaaccattataagctgcaataaacaagttaacaacaacaattgcattc attttatgtttcaggttcaggggagatgtgggaggttttttaaagcaag taaaacctctacaaatgtggta.

According to a preferred embodiment, the expression cassette comprises the following elements:

a) a promoter, preferably a human CMV promoter or a promoter derived from the human CMV promoter;
b) a 5'UTR polynucleotide sequence selected from the group consisting of a 5'UTR polynucleotide sequence comprising SEQ ID NO 1, a 5'UTR polynucleotide sequence comprising SEQ ID NO 2, a 5'UTR polynucleotide sequence comprising SEQ ID NO 3, a 5'UTR polynucleotide sequence comprising SEQ ID NO 4, a 5'UTR polynucleotide sequence comprising SEQ ID NO 5, a 5'UTR polynucleotide sequence comprising SEQ ID NO 6, a 5'UTR polynucleotide sequence comprising SEQ ID NO 7, and a 5'UTR polynucleotide sequence comprising a sequence that is at least 85%, preferably at least 90% identical to the sequence shown in SEQ ID NO 1, SEQ ID NO 2, SEQ ID NO 3, SEQ ID NO 4, SEQ ID NO 5, SEQ ID NO 6 or SEQ ID NO 7;
c) a polynucleotide encoding a hCD33 secretory leader sequence;
d) a polynucleotide encoding a polypeptide of interest or an insertion site for inserting a polynucleotide encoding a polypeptide of interest;
e) a 3'UTR polynucleotide sequence; and
f) a poly A site.

As described, % identity may be calculated over the whole length of the reference sequence. As discussed above and as is shown in the examples, the expression cassette according to the present invention results in an increased expression of the polypeptide of interest. A "polypeptide" refers to a molecule comprising a polymer of amino acids linked together by a peptide bond(s). Polypeptides include polypeptides of any length, including proteins (for example, having more than 50 amino acids) and peptides (for example, having 2-49 amino acids). Polypeptides include proteins and/or peptides of any activity or bioactivity. The polypeptide that is to be produced can be a pharmaceutically or therapeutically active compound, or a research tool to be utilized in assays and the like. A polypeptide is accordingly not limited to any particular polypeptide or group of polypeptides, but may on the contrary be any polypeptide, of any size, function or origin, which one desires to select and/or express by the methods described herein. Accordingly, several different polypeptides of interest may be expressed from the expression cassette according to the present invention and/or the host cells according to the present invention. As is outlined above, the term polypeptide include proteins and/or peptides of any activity or bioactivity, including e.g. bioactive polypeptides such as enzymatic proteins or peptides (e.g. proteases, kinases, phosphatases), receptor proteins or peptides, transporter proteins or peptides, bactericidal and/or endotoxin-binding proteins, structural proteins or peptides, immune polypeptides, immunoglobulins, toxins, antibiotics, hormones, growth factors, vaccines or the like. Said polypeptide may be selected from the group consisting of peptide hormones, interleukins, tissue plasminogen activators, cytokines, immunoglobulins, in particular antibodies or functional fragments or derivatives thereof and single domain antibodies, also referred to as nanobodies. According to one embodiment, the polypeptide of interest is glycosylated. The polypeptide of interest that is expressed from the expression cassette according to the present invention may also be a subunit or domain of one of the foregoing polypeptides, such as e.g. a heavy chain or a light chain of an antibody or a functional fragment or derivative thereof. In a preferred embodiment the polypeptide of interest is an immunoglobulin molecule, more preferably an antibody, or a subunit or domain thereof such as e.g. the heavy or light chain of an antibody or a single domain antibody. Also included are functional fragments or derivatives of the foregoing or a subunit or domain of the foregoing such as e.g. a heavy or light chain of an antibody or a functional fragment or derivative thereof. According to one embodiment, the polypeptide of interest is not hCD33.

The term "antibody" as used herein particularly refers to a protein comprising at least two heavy chains and two light chains connected by disulfide bonds. The term "antibody" includes naturally occurring antibodies as well as all recombinant forms of antibodies, e.g., humanized antibodies, fully human antibodies and chimeric antibodies. Each heavy chain is usually comprised of a heavy chain variable region (VH) and a heavy chain constant region (CH). Each light chain is usually comprised of a light chain variable region (VL) and a light chain constant region (CL). The heavy chain-constant region comprises three or—in the case of antibodies of the IgM- or IgE-type—four heavy chain-constant domains (CH1, CH2, CH3 and CH4) wherein the first constant domain CH1 is adjacent to the variable region and may be connected to the second constant domain CH2 by a hinge region. The light chain-constant region consists only of one constant domain. The variable regions can be further subdivided into regions of hypervariability, termed complementarity determining regions (CDRs), interspersed with regions that are more conserved, termed framework regions (FR), wherein each variable region comprises three CDRs and four FRs. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. The term "antibody" according to the invention, however, also includes other types and variants of antibodies such as heavy chain antibodies, i.e. antibodies only composed of one or more, in particular two heavy chains, and nanobodies, i.e. antibodies only composed of a single monomeric variable domain. Such nanobodies may also be linked to form multivalent structures. Preferably, the antibody is upon expression in the appropriate host cell glycosylated. As discussed above, the polynucleotide encoding the polypeptide of interest may also encode one or more subunits or domains of an antibody, e.g. a heavy or a light chain or a functional fragment or derivative, as polypeptide of interest.

A single-domain antibody, also referred to as nanobody is an antibody fragment consisting of a single monomeric variable antibody domain. Like a whole antibody, it is able to bind selectively to a specific antigen. With a molecular weight of only 12-15 kDa, single-domain antibodies are much smaller than common antibodies (150-160 kDa) which are composed of two heavy protein chains and two light chains, and even smaller than Fab fragments and single-chain variable fragments. The first single-domain antibodies were engineered from heavy-chain antibodies found in camelids; these are called $V_H H$ fragments. Heavy chain antibodies are also found in other species. An alternative approach is to split the dimeric variable domains from common immunoglobulin G (IgG) from humans or mice into monomers. Although most research into single-domain antibodies is currently based on heavy chain variable domains, nanobodies derived from light chains have also been shown to bind specifically to target epitopes. Antibody proteins obtained from members of the camel and dromedary family (*Camelus bactrianus* and *Camelus dromaderius*) including new world members such as llama species (*Lama paccos*, *Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals (see WO94/04678). A region of the camelid antibody which is the small single variable domain identified as $V_{HH}$ can be obtained by genetic engineering to yield a small protein having high affinity for a target, resulting in a low molecular weight antibody-derived protein known as a "camelid nanobody" (see U.S. Pat. No. 5,759,808; Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J 17: 3512-3520). Engineered libraries of camelid antibodies and antibody fragments are commercially available. As with other antibodies of non-human origin, an amino acid sequence of a camelid antibody can be altered recombinantly to obtain a sequence that more closely resembles a human sequence, i.e. the nanobody can be "humanized". Respective single-domain antibodies can also be expressed using the teachings of the present invention. Furthermore, as described, single-domain antibodies may also be linked to form multivalent structures. Respective multimeric nanobodies may also be expressed using the teachings of the present invention. According to one embodiment, a multimeric nanobody is expressed from a single expression cassette.

A "functional fragment or derivative" of an antibody in particular refers to a protein or glycoprotein which is derived from an antibody and is capable of binding to the same antigen, in particular to the same epitope as the antibody. The same applies mutatis mutandis for a fragment or derivative of an immunoglobulin molecule, a heavy chain or the light chain. It has been shown that the antigen-binding function of an antibody can be executed by fragments of a full-length antibody or derivatives thereof. Examples of fragments or derivatives of an antibody include (i) Fab fragments, monovalent fragments consisting of the variable region and the first constant domain of each the heavy and the light chain; (ii) F(ab)$_2$ fragments, bivalent fragments comprising two Fab fragments linked by a disulfide bridge at the hinge region; (iii) Fd fragments consisting of the variable region and the first constant domain CH1 of the heavy chain; (iv) Fv fragments consisting of the heavy chain and light chain variable region of a single arm of an antibody; (v) scFv fragments, Fv fragments consisting of a single polypeptide chain; (vi) (Fv)$_2$ fragments consisting of two Fv fragments covalently linked together; (vii) a heavy chain variable domain; and (viii) multibodies consisting of a heavy chain variable region and a light chain variable region covalently linked together in such a manner that association of the heavy chain and light chain variable regions can only occur intermolecular but not intramolecular. These antibody fragments and derivatives can be obtained using conventional techniques known to those with skill in the art.

As becomes apparent from the above described examples of polypeptides that can be expressed according to the teachings of the present invention, the final polypeptide that is to be produced and secreted by the host cell can also be a dimeric or multimeric protein. A preferred example of a respective protein is an immunoglobulin molecule, in particular an antibody that comprises e.g. heavy and light chains. There are several options for producing a respective dimeric or multimeric protein.

According to one embodiment, two or more subunits or domains of said dimeric or multimeric protein are expressed from one expression cassette according to the present invention. In this embodiment, one long transcript is obtained from the respective expression cassette that comprises the coding regions of the individual subunits or domains of the dimeric or multimeric protein. According to one embodiment, at least one IRES element (internal ribosomal entry site) is functionally located between the coding regions of the individual subunits or domains and each coding region is preceded by an hCD33 secretory leader sequence as described above. Thereby, it is ensured that separate translation products are obtained from said transcript and that the final dimeric or multimeric protein can be correctly assembled and secreted. Furthermore, also multimeric nanobodies can be expressed from a single expression cassette.

However, it is also within the scope of the present invention and for some embodiments it is even preferred to express the individual subunits or domains of a dimeric or multimeric protein from different expression cassettes. According to one embodiment, the expression cassette according to the present invention is a monocistronic expression cassette. In this embodiment, each expression cassette comprises a polynucleotide encoding one subunit or domain of the dimeric or multimeric protein as polypeptide of interest. According to one embodiment, all of these expression cassettes are designed according to the teachings of the present invention. However, it is also within the scope of the present invention to use different designs for different expression cassettes. After expression of the individual subunits/domains from the individual expression cassettes, the final dimeric or multimeric protein is assembled and secreted from the host cell. This embodiment will be explained in further detail in conjunction with the expression vector according to the present invention.

According to a preferred embodiment, the polynucleotide encoding the polypeptide of interest encodes as polypeptide of interest the heavy or the light chain of an antibody molecule or a functional fragment or derivative thereof.

According to one embodiment, the expression cassette according to the present invention already comprises a polynucleotide encoding at least part of a constant region of an immunoglobulin molecule. The polynucleotide encoding a corresponding variable part of the immunoglobulin molecule can then be inserted by the user/customer into the expression cassette by using appropriate cloning strategies in order to complete the expression cassette.

The expression cassette may comprise additional elements that can be used to alleviate and/or improve the selection of high expressing host cells. One established selection method known in the prior art for selecting host cells that express the polypeptide of interest with a high yield is based on the use of flow cytometry, in particular fluorescence activated cell sorting (FACS). Selection methods employing flow cytometry have the advantage that large numbers of cells can be screened rapidly. In one selection method that is particularly useful to identify high producing cell clones, a portion of the product of interest e.g. an antibody is expressed as membrane bound fusion polypeptide. Thereby, a portion of the product is displayed as fusion polypeptide on the cell surface. As the amount of produced fusion polypeptide correlates with the overall expression rate, the host cells can be selected via flow cytometry based upon the amount of fusion polypeptide displayed on the cell surface. This allows the rapid selection of high producing host cells. The expression cassette according to the present invention can be advantageously adapted so that it can be used in a respective selection method that is based on the use of flow cytometry. To allow efficient selection using flow cytometry, preferably FACS, a special expression cassette may be used for expressing the polypeptide of interest. Thus, according to one embodiment, the expression cassette for expressing the polynucleotide encoding the polypeptide of interest is designed such that a portion of the expressed polypeptide of interest, preferably less than 10%, more preferred less than 5% or even less than 2.5%, comprises a transmembrane anchor. Several options exist to achieve that result.

According to one embodiment, said expression cassette comprises additionally at least one stop codon downstream of the polynucleotide encoding the polypeptide of interest, and a further polynucleotide downstream of the stop codon encoding a membrane anchor and/or a signal for a membrane anchor. The respective elements are operatively linked. This design of the expression cassette has the effect that through translational read-through processes (the stop codon is "leaky") a portion of the polypeptide of interest is produced as a fusion polypeptide comprising a membrane anchor. As a result, this fusion polypeptide is displayed on the cell surface and cells displaying high levels of membrane-anchored fusion polypeptide can be selected by flow cytometry, preferably by FACS. Thereby, host cells are selected that have a high expression rate. Details and preferred embodiments of this stop codon based technology are described in WO2005/073375 and WO2010/022961. It is referred to this disclosure.

According to an alternative embodiment said expression cassette comprises downstream of the polynucleotide encoding the polypeptide of interest at least an intron comprising a 5' splice donor site and a 3' splice acceptor site and comprising an in frame translational stop codon and a polyadenylation signal and a polynucleotide downstream of said intron encoding a membrane anchor and/or a signal for a membrane anchor. The respective elements are operatively linked. This design of the expression cassette has the effect that through transcription and transcript processing at least two different mature mRNAs (mRNA-POI) and (mRNA-POI-ANCHOR) are obtained from the expression cassette. Translation of the mRNA-POI results in the product of interest. Translation of the mRNA-POI-ANCHOR results in a fusion polypeptide comprising the product of interest and a membrane anchor. As a result, this fusion polypeptide is again displayed on the cell surface and cells displaying high levels of membrane-anchored fusion polypeptide can be selected by flow cytometry, preferably FACS. Thereby, host cells are selected that have a high expression rate. Details and preferred embodiments of this intron based technology are described in WO2007/131774. It is referred to this disclosure.

According to a preferred embodiment which is in particular useful for the expression of antibodies as product of interest, the membrane anchor is an immunoglobulin transmembrane anchor. Other suitable membrane anchors and preferred embodiments of an immunoglobulin transmembrane anchor are described in WO2007/131774, WO2005/073375 and WO2010/022961. It is referred to the respective disclosure.

According to a second aspect, the present invention provides an expression vector for expressing a polypeptide of interest, comprising at least one expression cassette according to the first aspect of the present invention. Said expression cassette was described in detail above, it is thus referred to the above disclosure.

An "expression vector" according to the present invention in particular refers to a polynucleotide capable of carrying at least one foreign nucleic acid fragment. A vector functions like a molecular carrier, delivering fragments of nucleic acids respectively polynucleotides into a host cell. It comprises at least one expression cassette according to the first aspect of the present invention which comprises the necessary regulatory sequences for properly expressing a polynucleotide encoding a polypeptide of interest incorporated therein.

According to one embodiment, the expression vector additionally comprises at least one expression cassette comprising a polynucleotide encoding a selectable marker. Said expression cassette comprises the necessary regulatory sequences for properly expressing the polynucleotide encoding the selectable marker incorporated therein. Selectable markers include selectable markers that provide eukaryotic host cells with a resistance against toxic agents or drugs, such as antibiotics, in particular aminoglycoside antibiotics, e.g. a neomycin selectable marker. Selectable markers also include but are not limited to eukaryotic selectable markers such as dihydrofolate reductase (DHFR) and glutamine synthetase (GS). Other suitable selection markers such as the folic acid receptor are described in WO 2009/080759 and WO 2010/097240. Preferably, the expression vector comprises at least one expression cassette comprising a polynucleotide encoding an amplifiable selectable marker. An amplifiable, selectable marker allows the selection of a vector-containing eukaryotic host cells as well as gene amplification. A non-limiting example for an amplifiable, selectable mammalian marker gene is the dihydrofolate reductase (DHFR) gene. Other systems currently in use are among others the glutamine synthetase (gs) system (Bebbington et al., 1992) and the histidinol driven selection system (Hartmann and Mulligan, 1988). These amplifiable markers are also selectable markers and can thus be used to select those cells that obtained the vector. DHFR and glutamine synthetase provide good results. In both cases selection usually occurs in the absence of the appropriate metabolite (hypoxanthine and thymidine in case of DHFR, glutamine in the case of GS), thereby preventing growth of non-transformed cells. With amplifiable systems such as the DHFR system, expression of a recombinant protein can be increased by exposing the cells to certain agents promoting gene amplification such as antifolates (e.g. methotrexate (MTX)) in case of the DHFR system. A suitable inhibitor for GS promoting gene amplification is methionine sulphoximine (MSX). Exposure to MSX also results in gene amplification. According to a preferred embodiment, the expression vector comprises an expression cassette comprising a polynucleotide encoding a dihydrofolate reductase enzyme (DHFR) as selectable marker.

Furthermore, the expression vector may also comprise an expression cassette comprising a polynucleotide encoding a prokaryotic selectable marker. A "prokaryotic selectable marker" is a selectable marker allowing the selection in prokaryotic host cells under appropriate selection conditions. Examples of respective prokaryotic selectable markers are markers which provide a resistance to antibiotics such as e.g. ampicillin, kanamycin, tetracycline and/or chloramphenicol. Including a prokaryotic selectable marker in the expression vector has the advantage that the expression vector can be easily proliferated in prokaryotic host cells.

Preferably, the expression vector comprises at least one expression cassette according to the first aspect of the present invention, an expression cassette comprising a polynucleotide encoding a eukaryotic selectable marker that provides resistance against aminoglycoside antibiotics, preferably a neo selectable marker, and an expression cassette comprising a polynucleotide encoding an amplifiable selectable marker, preferably DHFR.

The expression vector according to the present invention can comprise more than one expression cassette for expressing a polypeptide of interest. Therefore, according to one embodiment several expression cassettes for expressing the same or different polypeptides of interest are arranged on the expression vector according to the present invention. Hence, the present invention also provides an expression vector comprising more than one expression cassette wherein each expression cassette encodes e.g. a subunit or domain of a dimeric or higher order multimeric protein. Expression cassettes encoding different subunits of a multimeric protein, each incorporated in a different expression cassette can be placed e.g. adjacent to each other. For multimeric proteins encoded by at least two distinct genes (for instance, the light and heavy chains of an antibody or functional fragments or derivatives thereof), the polynucleotides encoding the desired subunits or domains are inserted as polypeptides of interest into the different expression cassettes. A respective embodiment using at least two distinct expression cassettes for expressing individual subunits or domains of a dimeric or multimeric protein as polypeptide of interest is particularly advantageous for expressing immunoglobulin molecules such as e.g. antibodies. In the host cell, the dimeric or multimeric protein, e.g. the antibody is assembled and secreted. According to one embodiment, the expression cassette design according to the present disclosure is used for expressing the heavy chain of an antibody. The expression cassette of the light chain may have in embodiments a different design, e.g. it may comprise a different secretory leader sequence such as e.g. an Ig leader sequence. According to one embodiment, both expression cassettes are designed according to the teachings of the present disclosure.

Thus, according to one embodiment, the expression vector comprises at least two expression cassettes according to the first aspect of the present invention. The polynucleotide comprised in one of said expression cassettes encodes the heavy chain of an immunoglobulin molecule or a functional fragment or derivative thereof as polypeptide of interest and the polynucleotide comprised in the other expression cassette encodes the light chain of an immunoglobulin molecule or a functional fragment or derivative thereof as polypeptide of interest. Upon expression of the light chain and the heavy chain from said expression cassettes in the host cell, the functional immunoglobulin molecule, which preferably is an antibody, is assembled and secreted from the host cell. According to one embodiment, the 5' UTR for the light chain or a functional fragment or derivative thereof comprises or consists of the SEQ ID NO 3. According to one embodiment, the 5' UTR for the heavy chain or a functional fragment or derivative thereof comprises or consists of SEQ ID NO 1 or SEQ ID NO 4. According to one embodiment, the 5' UTR for the light chain or a functional fragment or derivative thereof comprises or consists of the SEQ ID NO 5. According to one embodiment, the 5' UTR for the heavy chain or a functional fragment or derivative thereof comprises or consists of SEQ ID NO 6 or SEQ ID NO 7.

Suitable expression vectors that can be used in conjunction with the present invention are described in WO 2009/080720, wherein, however, in the teachings of the present invention the immunoglobulin secretory leader sequence taught by WO 2009/080720 is replaced by the hCD33 secretory leader sequence in the expression cassette(s) comprising the polynucleotide encoding the polypeptide of interest. As described, in case more than one expression cassette is present in the expression vector, it is sufficient that one expression cassette is designed as described herein.

According to a third aspect, a eukaryotic host cell is provided, comprising at least one expression cassette according to the first aspect of the present invention and/or comprising at least one expression vector according to the second aspect of the present invention. The expression cassette and the expression vector according to the present invention was described in detail above, it is referred to the above disclosure which also applies here. Preferably, the expression cassette' comprises a polynucleotide encoding a polypeptide of interest. A respective expression cassette preferably comprised in an expression vector can be introduced into the host cell by transfection.

According to one embodiment, the eukaryotic host cell comprises at least two expression cassettes according to the present invention. According to one embodiment each of said expression cassettes comprises a polynucleotide encoding at least one subunit or domain of a dimeric or multimeric protein as polypeptide of interest. This embodiment is particularly suitable for expressing immunoglobulin molecules. According to a preferred embodiment, the host cell comprises a first expression cassette according to the first aspect of the present invention, which comprises a polynucleotide encoding the heavy chain of an immunoglobulin molecule or a functional fragment or derivative thereof as polypeptide of interest and a second expression cassette according to the first aspect of the present invention, which comprises a polynucleotide encoding the light chain of an immunoglobulin molecule or a functional fragment or derivative thereof as polypeptide of interest. As discussed above, preferably, the 5'UTR that is used in the expression cassette for expressing the light chain comprises or consists of SEQ ID NO 3 and the 5'UTR that is used in the expression cassette for expressing the heavy chain comprises or consists of SEQ ID NO 1 or SEQ ID NO 4. According to one embodiment, the 5'UTR that is used in the expression cassette for expressing the light chain comprises or consists of SEQ ID NO 5 and the 5'UTR that is used in the expression cassette for expressing the heavy chain comprises or consists of SEQ ID NO 6 or SEQ ID NO 7. Said expression cassettes can be introduced into the host cells by using one or more appropriate expression vector(s) as described above. According to one embodiment, the first expression cassette was introduced by one expression vector and the second expression cassette was introduced by a second expression vector. However, it is preferred that both expression cassettes were introduced by using one expression vector which carries both expression cassettes.

According to one embodiment, the eukaryotic host cell comprises at least one expression cassette according to the first aspect for expressing the heavy chain of an antibody. As described, e.g. a 5'UTR comprising or consisting of SEQ ID NO 1, 4, 6 or 7 may be used for this purpose.

Basically any eukaryotic host cells can be used in conjunction with the present invention as long as they allow the efficient expression of a polypeptide from the expression cassette according to the present invention. Preferably, the eukaryotic host cell is a mammalian cell. Said mammalian cell preferably is selected from the group consisting of rodent cells, human cells and monkey cells. Particularly preferred is the use of rodent cells, preferably selected from the group consisting of CHO cells, BHK cells, NSO cells, mouse 3T3 fibroblast cells, and SP2/0 cells. Particularly preferred is the use of CHO cells as host cells. Human cells can be e.g. selected from the group consisting of HEK293 cells, MCF-7 cells, PerC6 cells and HeLa cells. Monkey cells can be selected e.g. from COS cells and Vero cells. The expression vector according to the present invention is particularly suitable for producing polypeptides in rodent cells such as CHO cells, including DHFR" CHO cells or DHFR$^+$ CHO cells. Preferably, the host cell is a CHO cell.

According to a fourth aspect, a method is provided for producing the host cell according to the third aspect of the present invention, wherein the expression vector according to the second aspect of the present invention is introduced into the eukaryotic host cell, which preferably is a mammalian host cell. Thereby, the expression cassette according to the first aspect which preferably comprises a polynucleotide for expressing a polypeptide of interest is introduced into the host cell.

Introduction may be achieved e.g. by transfecting the expression vector according to the second aspect of the present invention. According to one embodiment, the expression vector integrates into the genome of the host cell (stable transfection). Suitable expression vectors allowing the introduction of the expression cassette according to the first aspect of the present invention into the host cell are described in detail above in conjunction with the second aspect according to the present invention. If the introduced expression cassette is not inserted into the genome (transient transfection) it can be lost at the later stage e.g. when the cells undergo mitosis. Suitable expression vectors might also be maintained in the host cell without integrating into the genome, e.g. by episomal replication. There are several appropriate methods known in the prior art for introducing an expression vector into a eukaryotic host cell, including mammalian host cells, in particular by transfection. Respective methods include but are not limited to calcium phosphate transfection, electroporation, lipofection, biolistic- and polymer-mediated genes transfer. Besides traditional random integration based methods also recombination mediated approaches can be used. Such recombination methods may include use of site specific recombinases like Cre, Flp or ΦC31 (see e.g. Oumard et al, Cytotechnology (2006) 50: 93-108) which can mediate directed insertion of transgenes. Alternatively, the mechanism of homologous recombination might be used to insert the expression cassette according to the present invention (reviewed in Sorrell et al, Biotechnology Advances 23 (2005) 431-469). Recombination based gene insertion allows to minimize the number of elements to be included in the expression vector that is introduced to the host cell. Embodiments of a suitable expression vector or combinations of expression vectors according to the present invention as well as suitable host cells are described in detail above; it is referred to the above disclosure. As discussed above in conjunction with the embodiment the expression cassettes comprising the polynucleotides encoding the heavy chain and the light chain of an immunoglobulin molecule or a functional fragment or derivative thereof may be located on the same or on different expression vectors in case a combination of at least two expression vectors is used for transfecting the host cells.

According to a fifth aspect a method is provided for producing a polypeptide of interest, said method comprising culturing host cells according to the third aspect of the present invention in a cell culture under conditions allowing the expression of said polypeptide of interest. There are two main formats of host cell cultures, namely cultures of adherent cells and suspension cultures. The use of suspension cultures is preferred. According to one embodiment, said host cells are cultured under serum-free conditions.

The polypeptide of interest is expressed from the expression cassette according to the present invention and is secreted from the host cell, e.g. into the culture medium, and the secreted polypeptide can be obtained therefrom. If more then one expression cassette is present in the host cell e. g. when the dimeric or multimeric protein is expressed (see above), the dimeric or multimeric protein is assembled in the cell and is then secreted from the host cell. Due to the extraordinary expression that is achieved by using the novel 5'UTR/secretory leader sequence combination according to the present invention, polypeptides can be expressed and secreted with high yield. The secreted polypeptide may also be subject to further processing steps such as e.g. purification and/or modification steps. Accordingly, the method for producing the polypeptide of interest may comprise at least one of the following steps:

isolating the polypeptide of interest from said cell culture medium; and/or processing the isolated polypeptide of interest.

Thus, the polypeptide produced in accordance with the invention may be recovered and optionally further processed, e.g. further purified, isolated and/or modified by methods known in the art. For example, the polypeptide may be recovered from the nutrient medium by conventional procedures including, but not limited to, centrifugation, filtration, ultra-filtration, extraction or precipitation. Purification may be performed by a variety of procedures known in the art including, but not limited to, chromatography (e.g. ion exchange, affinity, hydrophobic, chromatofocusing, and size exclusion), electrophoretic procedures (e.g., preparative isoelectric focusing), differential solubility (e.g. ammonium sulfate precipitation) or extraction.

As discussed above, the polypeptide of interest is preferably an immunoglobulin molecule or functional fragment or derivative thereof, more preferably an antibody or a functional fragment or derivative thereof.

According to a sixth aspect, the present invention pertains to the use of a 5'UTR sequence in combination with a hCD33 secretory leader sequence in an expression cassette for expressing a polypeptide of interest with high yield from said expression cassette, wherein said 5'UTR polynucleotide sequence is selected from the group consisting of a 5'UTR polynucleotide sequence comprising SEQ ID NO 1, a 5'UTR polynucleotide sequence comprising SEQ ID NO 2, a 5'UTR polynucleotide sequence comprising SEQ ID NO 3, a 5'UTR polynucleotide sequence comprising SEQ ID NO 4 and a 5'UTR polynucleotide sequence comprising a sequence that is at least 85%, preferably at least 90% identical to the sequence shown in SEQ ID NO 1, SEQ ID NO 2, SEQ ID NO 3 or SEQ ID NO 4 or wherein said 5'UTR polynucleotide sequence is selected from the group consisting of a 5'UTR polynucleotide sequence comprising SEQ ID NO 5, a 5'UTR polynucleotide sequence comprising SEQ ID NO 6, a 5'UTR polynucleotide sequence comprising SEQ ID NO 7 and a 5'UTR polynucleotide sequence comprising a sequence that is at least 85%, preferably at least 90% identical to the sequence shown in SEQ ID NO 5, SEQ ID NO 6 or SEQ ID NO 7. The identity may be calculated over the whole length of the reference sequence.

The advantages of a respective combination, suitable and preferred embodiments of the 5'UTR polynucleotide sequence and the hCD33 secretory leader sequence as well as suitable and preferred embodiments of the expression cassette and the polynucleotide encoding the polypeptide of interest are described in detail above. It is referred to the above disclosure which also applies here.

Preferably, the expression cassette has the design of the expression cassette that is described above in conjunction with the first aspect of the present invention. It is referred to the above disclosure. According to one embodiment, the expression cassette has one or more of the following characteristics:

a) it comprises a promoter;
b) it comprises a 5' UTR polynucleotide sequence as described above;
c) it comprises a hCD33 secretory leader sequence which comprises and preferably consists of the sequence MPLLLLLPLLWAGALA (SEQ ID NO 12);
d) it comprises a polynucleotide encoding a polypeptide of interest or an insertion site for inserting a polynucleotide encoding a polypeptide of interest;
e) it comprises a 3'UTR sequence and/or
f) it comprises a poly A site Details with respect to the individual elements and preferred embodiments and combinations are described above in conjunction with the first aspect of the present invention. It is referred to the above disclosure.

According to one embodiment, the polynucleotide encoding the polypeptide of interest encodes as polypeptide of interest two or more subunits or domains of a dimeric or multimeric protein, wherein at least one IRES element is located between the coding regions of the individual subunits or domains and each coding region is preceded by an hCD33 secretory leader sequence. However, the use of monocistronic expression cassettes is preferred in the context of the present invention.

According to an alternative embodiment, the polynucleotide encoding the polypeptide of interest encodes as polypeptide of interest a subunit or domain of a dimeric or multimeric protein. Preferably, the polynucleotide encoding the polypeptide of interest encodes as polypeptide of interest the heavy or the light chain of an antibody molecule or a functional fragment or derivative thereof. According to one embodiment, an expression cassette design according to the present disclosure is used for expressing the heavy chain of an antibody. Here, the expression cassette for expressing the light chain may have a different design and may, e.g., comprise a different leader sequence, e.g. a Ig leader sequence, or may also be designed according to the teachings of the present invention. According to one embodiment, an expression cassette design according to the present disclosure is used for expressing the light chain of an antibody. Here, the expression cassette for expressing the heavy chain may have a different design and may, e.g., comprise a different leader sequence, e.g. a Ig leader sequence, or may also be designed according to the teachings of the present invention.

According to one embodiment, subject-matter described herein as comprising certain elements also refers to subject-matter consisting of the respective elements. In particular, the 5'UTRs described herein as comprising certain sequences may also consist of the respective sequences.

It is preferred to select and combine preferred embodiments described herein and the specific subject-matter arising from a respective combination of preferred embodiments also belongs to the present disclosure.

The full content of the texts and documents as mentioned herein are incorporated herein by reference and thus form part of the present disclosure.

The following examples serve to illustrate the present invention without in any way limiting the scope thereof. In particular, the examples relate to preferred embodiments of the present invention.

EXAMPLES

The examples were performed according to the following protocol:

Example A

I. Material and Methods

Host Cells

As host cells, CHO (Chinese Hamster Ovary) cells derived from CHO-K1 cells are used.

Expression Vectors

As standard control an expression vector having a design as described in WO 2009/080720 (see in particular example 6) is used, which utilizes an Ig secretory leader sequence in the expression cassettes for expressing the antibody light and heavy chains. The CMV promoter comprised SEQ ID NO 8. SEQ ID NO 3 is used as 5'UTR for expressing the light chain and SEQ ID NO 4 was used as 5'UTR for expressing the heavy chain. An expression vector according to teachings of the present invention is obtained from said control vector by replacing the existing light- and heavy-chain immunoglobulin secretory leader sequence by the following hCD33 secretory leader sequence:

(SEQ ID NO 12)
MPLLLLLPLLWAGALA

Said expression vectors are used in order to express antibody molecules. A corresponding vector design is also used in order to express a nanobody as polypeptide of interest, wherein, however, the 5'UTR according to SEQ ID NO 5 was used. Here, however, only one expression cassette is needed. The control vector had the same design, however, again a Ig leader sequence was used.

Cell Culturing, Transfection and Selection

Cells are cultured using proprietary in-house cell culture medium, and regularly passaged 2-3 times a week to maintain in logarithmic growth phase throughout the study. The cells are transfected using standard nucleofection method. 5E6 cells/nucleofection impulse are centrifuged and resuspended in transfection buffer. 3 ug vector DNA coding for the polypeptide of interest are added, and nucleofection is performed. Transfected cells are transferred in 125 ml shake flask, and are cultivated in shaking conditions for 24-48 hours.

A first selection step with G-418 is performed as previously described in WO 2009/080720. Further selection is performed with 2 additional methotrexate (MTX) selection steps, namely 500 nM MTX, and 1000 nM MTX. Selected pools, comprising of resistant, mostly good producing cells are cloned at a density 0.5-1 cell/well, either by limiting dilution, or using FACS system. For obtained clones, clonal productivity and growth are analysed in different screening formats.

II. Results

The experimental data obtained with the expression vector according to the prior art (control expression vector) comprising the Ig secretory leader sequence and the expression vector according to the present invention comprising the hCD33 secretory leader sequence demonstrate that the produced antibody titer is remarkable increased when using the novel combination of the specific 5'UTR and the hCD33 secretory leader sequence according to the present invention. As protein of interest, an IgG antibody was expressed. The observed productivity increase on the pool level was on average 2.88 fold when using the expression vector according to the present invention. The results could be further improved on the clone level, wherein a productivity increase of 4.1 fold could be obtained when using the expression vector according to the present invention (when comparing the best control clone obtained with the control expression vector and the best clone obtained with the expression vector according to the present invention).

When expressing a nanobody as protein of interest, comparison of the best clones shows a productivity increase of 1.1 fold when using the expression vector according to the present invention and when comparing 6 best clones a productivity increase of 1.6 fold on average was obtained. This is illustrated by the following tables:

TABLE 2

Novel combination evaluation with IgG antibody: A 2.88 fold productivity increase is achieved on the pool level with the expression vector according to the present invention.

| Titer (g/L) | G-418 | 1000 nM MTX |
| --- | --- | --- |
| hCD33 signal peptide | 0.006 | 0.094 |
| Ctrl. | 0.005 | 0.038 |

TABLE 3

Novel combination evaluation with IgG antibody: 4.1 fold productivity increase comparing the best clones of the expression vector known in the prior art and the expression vector according to the present invention and in average of 6 best clones: 4 fold productivity increase

| | hCD33 Top 6 clones | Control Top 6 clones |
| --- | --- | --- |
| Titer (g/L) | 2.99 | 0.727 |
| | 2.69 | 0.656 |
| | 2.65 | 0.642 |
| | 2.21 | 0.622 |
| | 2.12 | 0.575 |
| | 2.11 | 0.503 |

TABLE 4

Novel combination evaluation with nanobodies: 1.1 fold productivity increase comparing the best clones of the expression vector known in the prior art and the expression vector according to the present invention and in average of 6 best clones: 1.6 fold productivity increase.

| | hCD33 SP Top 6 clones | Control Top 6 clones |
| --- | --- | --- |
| Titer (g/L) | 0.92 | 0.75 |
| | 0.92 | 0.58 |
| | 0.90 | 0.57 |
| | 0.88 | 0.57 |
| | 0.88 | 0.57 |
| | 0.87 | 0.57 |

Example B

Expression Vectors

As standard control the expression vectors having the basic design as described in WO 2009/080720 (see in particular example 6) were used, which utilize Ig secretory leader sequences in the expression cassettes for expressing the antibody light and heavy chains. The expression cassette for the heavy chain was modified using the leaky stop codon technology described in WO2010/022961 to facilitate FACS selection. The CMV promoter comprised SEQ ID NO 8. SEQ ID NO 5 is used as 5'UTR for expressing the light chain and SEQ ID NO 7 is used as 5'UTR for expressing the heavy chain. An expression vector according to teachings of the present invention is obtained from said control vectors by replacing the existing heavy-chain immunoglobulin secretory leader sequence by the following hCD33 secretory leader sequence:

```
                                         (SEQ ID NO 12)
MPLLLLLPLLWAGALA
```

Said expression vectors are used in order to express different antibody molecules.

The evaluation was performed to address IgG expression and correct signal peptide (leader sequence) processing on the heavy chain cassette for 3 different antibodies. The correct processing of the leader sequence, i.e. leader sequence cleavage by the signal peptidase, is essential to obtain the expected sequence of the polypeptide of interest at its N-terminus, and thus a functional molecule with the expected quality. It was noted previously that in some cases using prior art designs the processing of the signal peptide was incorrect, and generated e.g. the heavy or light chain with one or more additional amino acids at the N-terminus. Depending on the one or more amino acids which incorrectly remained at the N-terminus, this extension of the amino acid sequence by the remaining one or more amino acids of the leader sequence can e.g. increase aggregation propensity of molecule or induce disulphide bond formation. Thus, it may have a severe impact on product quality. Furthermore, it was found that incorrect signal peptide processing poses the risk that the polypeptide of interest, such as an antibody product, is cleaved by protease downstream from the predicted cleavage site at N-terminus (also referred to as clipping). This generates a truncated product, which also might have a severe impact on the molecule quality.

Table 5 illustrates the signal peptide (leader sequence) processing results obtained with the technology of the present disclosure compared to the controls. As can be seen, using the technology of the invention significantly reduced unwanted signal peptide processing and thus improved the quality.

TABLE 5

Evaluation of different signal peptides on the heavy chain cassette shows improved and correct cell line processing when expressing three different model antibodies

| Polypeptide of interest | Signal peptide processing/extensions and clipping with hCD33 | Signal peptide processing/extensions and clipping with other signal peptides |
|---|---|---|
| Antibody 1 | <1% | ~3.6% |
| Antibody 2 | <1% | ~3.2% |
| Antibody 3 | None | ~1.5% |
|  |  | ~1.2% |

---

The invention claimed is:

1. An expression cassette suitable for expressing a polypeptide of interest comprising:
   a) a promoter;
   b) a 5'UTR polynucleotide sequence, wherein said 5'UTR polynucleotide sequence is selected from the group consisting of
      i) a 5'UTR polynucleotide sequence comprising the following sequence (SEQ ID NO 6)
   agatcgcctggagacgccatccacgctgttttgacctccatagaagacac cgggaccgatccagcctccgcggccgggaacggtgcattggaacgcggat tccccgtgccaagagtgacgtaagtaccgcctatagagtctataggccca cccccttggcttcgttagaacgcggctacaattaatacataaccttatgt atcatacacatacgatttaggtgacactatagaataacatccactttgcc tttctctccacaggtgtccactcccaggtccaactgcacctcggttctat cgaaaaacgcgtgccgccacc;
   and
      ii) a 5'UTR polynucleotide sequence comprising the following sequence (SEQ ID NO 7)
   agatcgcctggagacgccatccacgctgttttgacctccatagaagacac cgggaccgatccagcctccgcggccgggaacggtgcattggaacgcggat tccccgtgccaagagtgacgtaagtaccgcctatagagtctataggccca cccccttggcttcgttagaacgcggctacaattaatacataaccttatgt atcatacacatacgatttaggtgacactatagaataacatccactttgcc tttctctccacaggtgtccactcccaggtccaactgcacctcggttctat cgaaaacgcgtgccgccacc;

c) a polynucleotide encoding a hCD33 secretory leader sequence; and
   d) a polynucleotide encoding a polypeptide of interest or an insertion site for inserting a polynucleotide encoding a polypeptide of interest.

2. The expression cassette of claim 1, wherein the hCD33 secretory leader sequence consists of the sequence MPLLLLLPLLWAGALA (SEQ ID NO: 12).

3. The expression cassette of claim 1, wherein said expression cassette further comprises e) a 3'UTR sequence and/or
   f) a poly A signal.

4. The expression cassette of claim 1 wherein the polynucleotide encoding the polypeptide of interest encodes as polypeptide of interest, two or more subunits or domains of a dimeric or multimeric protein, wherein at least one IRES element is located between the coding regions of the individual subunits or domains and each coding region is preceded by an hCD33 secretory leader sequence.

5. An expression vector for expressing a polypeptide of interest, comprising at least one expression cassette of claim 1, additionally comprising one or more of the following elements:
   a) at least one expression cassette comprising a polynucleotide encoding a selectable marker;
   b) at least one second expression cassette for expressing a polypeptide of interest.

6. A eukaryotic host cell comprising at least one expression cassette of claim 1.

7. The host cell of claim 6, wherein said host cell is selected from the group consisting of rodent cells, primate cells and human cells and wherein said host cell preferably is a CHO cell.

8. A method for producing a polypeptide of interest, said method comprising culturing the eukaryotic host cells of claim 6 in a cell culture under conditions allowing expression of said polypeptide of interest.

9. The method of claim 8, wherein said polypeptide of interest is secreted into the cell culture medium and is isolated from the cell culture medium and the isolated polypeptide is optionally further processed.

10. The method of claim 8, wherein said polypeptide is an immunoglobulin molecule or fragment thereof.

11. The expression cassette of claim 1, wherein the polynucleotide encoding the polypeptide of interest encodes as polypeptide of interest, two or more subunits or domains of a dimeric or multimeric protein, wherein at least one IRES element is located between the coding regions of the individual subunits or domains and each coding region is preceded by an hCD33 secretory leader sequence.

12. The expression cassette of claim 1, wherein the expression cassette is a monocistronic expression cassette.

13. The expression cassette of claim 1 wherein the 5'UTR polynucleotide sequence comprises SEQ ID NO: 6.

14. The expression cassette of claim 1 wherein the 5'UTR polynucleotide sequence comprises SEQ ID NO: 7.

* * * * *